United States Patent [19]

Forde

[11] Plant 4,405

[45] Apr. 10, 1979

[54] WALNUT TREE

[75] Inventor: Harold I. Forde, Davis, Calif.

[73] Assignee: The Regents of the University of California, Berkeley, Calif.

[21] Appl. No.: 898,596

[22] Filed: Apr. 21, 1978

[51] Int. Cl.[2] ..... A01H 5/03

[52] U.S. Cl. ..... Plt./32

[58] Field of Search ..... Plt./32

*Primary Examiner*—Robert E. Bagwill
*Assistant Examiner*—James R. Feyrer

[57] ABSTRACT

A new and distinct variety of *Juglans regia* characterized in having semi-upright growth, moderate vigor and early, heavy production; and a distinguishing short, elliptical nut shape. The medium textured, light colored shell is well sealed, having a kernel percentage average of about 54 percent.

2 Drawing Figures

This invention relates to a new and distinct cultivar of walnut tree, botanical classification *Juglans regia.* The original tree grew from a seed from the University of California Walnut Breeding Program, in 1964.

A continuous walnut breeding program has been maintained by the University of California from 1948 to the present time. In 1963, pistillate flowers of the cultivar Pedro were bagged and pollinated with pollen from U.C. Selection 56-224. This selection grew from one of the resulting seeds, therefore, the parents of this selection are Pedro and U.C. Selection 56-224. Pedro, was released as a cultivar from the University of California Walnut Breeding Program by E. F. Serr and Harold I. Forde in 1968. Pedro resulted from crossing Conway Mayette × Payne in 1952. U.C. 56-224 resulted from the cross Sharkey × Marchetti in 1955.

Thirty-three seedlings of the cross Pedro × 56-224 were established in the test orchard on the campus of the University of California, Davis. The resulting seedlings were maintained under careful and continuous observation. When such seedlings bore fruit, one which is the instant cultivar, evidenced novel and commercially desirable characteristics, and was selected for asexual reproduction to permit further testing and possible introduction to the trade.

After its origin, as above, this cultivar named "Howard," was asexually reproduced by top grafting on trees, of the two common rootstocks, Northern California black walnut *Juglans hindsii* and Paradox *J. hindsii* × *J. regia,* in the University of California (Department of Pomology) experimental orchard. Subsequently, it was also asexually propagated by grafting and budding in test plots in some of the walnut growing areas of California. The trees, leaves, and fruit resulting from such reproductions all ran true to the parent trees in every respect.

Figure 1:
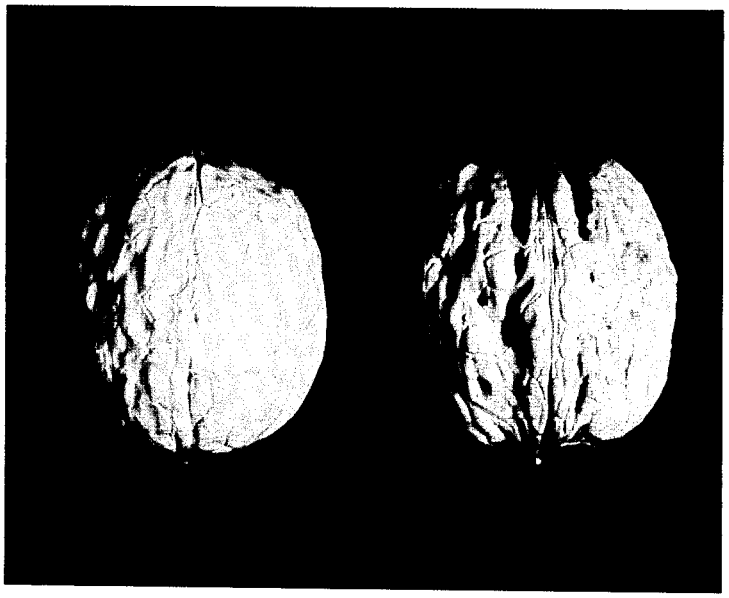
FIG. 1 illustrates two views of nuts in the shell which are typical of the new variety.
Figure 2:
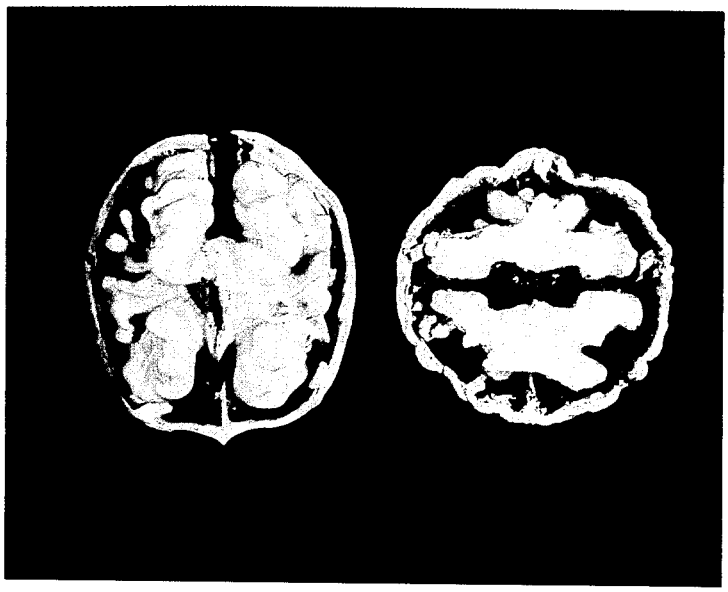
FIG. 2 illustrates the nut in cross section and in longitudinal view with half the shell removed.
Figure 3:
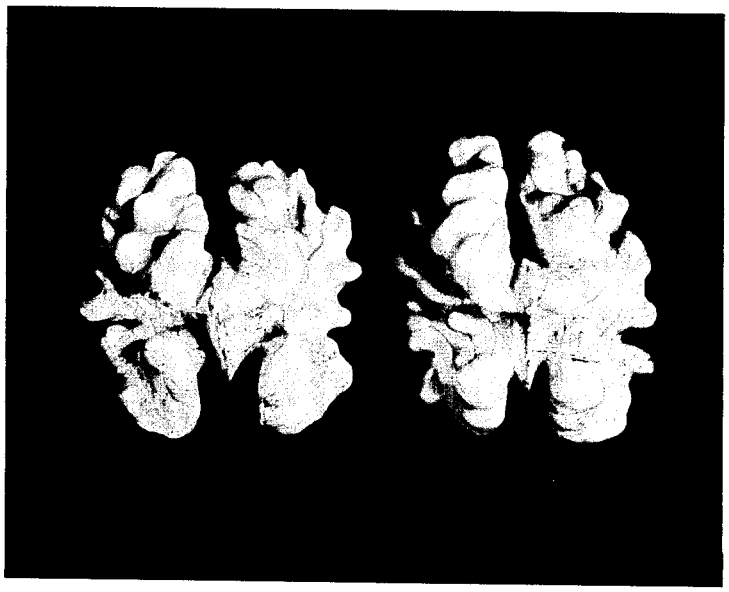
FIG. 3 illustrates kernel halves of the nut of the new variety.

This new and distinct cultivar of walnut tree is characterized by its semi-upright growth, moderate vigor and early and heavy production. Nearly all shoots from the terminal buds and about 80 percent of the shoots from axillary buds produce pistillate flowers. The start of growth and leafing is about the same time as that of Hartley and the nuts are ready for harvest about four or five days before Hartley.

A particularly distinguishing feature of the new variety is its lateness in both start of growth and harvest with such a high percentage of lateral buds flowering as compared to the other cultivars now in use. While the cultivar 64-172 (Chandler) starts its growth about the same time as this variety, it has as many lateral bud flowers, Chandler is ready to harvest about five days later than this variety.

A principal distinguishing characteristic of the present cultivar is the shape of the nut. The nut is elliptical with the ellipse being quite short in relation to diameter and both ends are somewhat flattened. The shell is light colored with a medium texture and is well sealed. Well grown lots of nuts of this variety produce kernels most of which are light and light amber and some of which are amber in color. Kernel percent averages about 54 percent.

The botanical details of this new and distinct cultivar are as follows:

Tree: Size, medium (similar to Ashley or Vina); vigor, moderately vigorous; growth, semi-upright tree, tends to be a little taller than it is wide. Round top with slight tendency to conical shape; production, very productive; bearing, early regular bearer.

Trunk and Branches: Like most other *J. regia.*

Old bark light gray and smooth, very old bark would probably roughen as it does in other walnuts. New shoots have green bark which turns brown as the season progresses, this is also like other walnuts.

Leaves: Leaves are pinnately compound with 5 to 9 leaflets per leaf. Leaves are green with lower surface being lighter green than the top.

Leaves vary in length from about 20 to 40 cm., averaging about 31 cm. Leaflets vary in length from about 5 to 18 cm., averaging about 14 cm. and in width from about 3 to 9 cm., averaging about 6.0 cm. The basal leaflets are smaller with the terminal leaflet and the leaflets next to it being the largest.

Leaflet shape is elongated ovate. Leaflets have acute apices and rounded or uneven bases. Uneven bases have blade on one side of the mid-rib 2 to 5 mm. farther from the rachis than it is on the other side.

Leaf texture, smooth; margin, smooth; venation, pinnate.

Start of growth, leafing date, is mid-season having been 12 to 21 days after Payne, averaging 13 days after Payne. This is practically the same leafing time as Hartley.

Inflorescence: This cultivar is very precocious, young grafted trees having produced pistillate flowers at two years of age and catkins at three. About 80 percent of the axillary (lateral) buds produce pistillate flowers.

Full bloom of pistillate flowers has been 31 to 47 days after leafing date of Payne, averaging 38 days after Payne. First pollen shedding has been 15–29 days after Payne leafing with the average being 20 days after Payne. Last pollen shedding has been 24 to 43 days after Payne leafing with an average of 34 days. Calendar dates in 1976 were pistillate full bloom, April 21; first pollen shed March 31; and last pollen shed April 19. The trees have produced many catkins. Most flowering tips have two pistillate flowers, some have three, a few have one and a few have more than three. There is nothing distinctive about the form or color of the male or female as they are similar to most other walnut flowers.

Harvest: Nuts of this cultivar are ready to harvest about 10 days after Payne which is about 4 or 5 days earlier than Hartley. No other cultivar now in use, which starts growth and matures its nuts as late as this cultivar, has as high a percentage of axillary buds producing pistillate flowers.

The Fruit: The green fruit before it is ready to harvest is almost spherical in shape, the length being only 2 or 3 mm. more than the diameter. The hull is green with small lenticals and is of about average thickness, the hull is similar in appearance and thickness to the hull of the Payne variety.

The Nut and the Shell: The kernel color refers to standard U.S. Department of Agriculture grading chart.

The shape of the nut in longitudinal section is nearly elliptical, the ellipse being short in relation to its width. An average well-grown nut would have a length of about 40 mm., a suture diameter of about 36 mm. and a cheek diameter of about 38 mm. View with the suture up shows some flattening at both ends.

The nut shell is medium light colored and of medium texture having longitudinal grooves and some irregular pitting. Many of the nuts have a fairly deep pit on one side of the suture, a few have the pit on both sides of the suture. The nut shell is of medium thickness and is well filled and well sealed. The kernel is plump. In 1976, a 500 gr. random sample from the plot at Davis contained 36 nuts and based on total in-shell weight, had 23 percent light, 21 percent light amber, 11 percent amber and 1 percent off-grade for a total of 56 percent kernel. Percent light in other samples has varied from about 20 to 50 percent with an average of about 35 percent. Percent kernel has varied from 51 to 56 percent with an average of about 54 percent.

I claim:

1. The new and distinct variety of walnut tree herein described and illustrated and characterized by its semi-upright growth, moderate vigor, heavy production and early harvest; said variety having its start of growth about the same time as Hartley and its harvest about 4 or 5 days before Hartley; said variety being further characterized by its production of pistillate flowers on nearly all shoots from terminal buds and on about 80 percent from shoots of axillary buds; said percent being substantially higher than other varieties currently in use and which have the same starting growth and nut maturity, and being about the same as U.C. 64-172; said variety being primarily characterized by its nuts, the ends of which are somewhat flattened and which are elliptical in longitudinal cross section with the ellipse being quite short in relation to diameter; said nuts having a shell light in color, medium in texture which is well filled and sealed.

* * * * *